US010045929B2

(12) United States Patent
Jegou et al.

(10) Patent No.: US 10,045,929 B2
(45) Date of Patent: Aug. 14, 2018

(54) METHOD FOR TREATING KERATIN FIBRES WITH AN AMINO POLYMER AND AN ACTIVATED ESTER

(71) Applicant: L'OREAL, Paris (FR)

(72) Inventors: Gwenaëlle Jegou, Saint Michel sur Orge (FR); Nawel Baghdadli, Massy (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 15/121,134

(22) PCT Filed: Feb. 20, 2015

(86) PCT No.: PCT/FR2015/050412
§ 371 (c)(1),
(2) Date: Aug. 24, 2016

(87) PCT Pub. No.: WO2015/128566
PCT Pub. Date: Sep. 3, 2015

(65) Prior Publication Data
US 2017/0007528 A1  Jan. 12, 2017

(30) Foreign Application Priority Data
Feb. 26, 2014 (FR) ...................... 14 51536

(51) Int. Cl.
A61K 8/36 (2006.01)
A61K 8/84 (2006.01)
A61Q 5/00 (2006.01)
A61K 8/49 (2006.01)
A61K 8/81 (2006.01)
A61K 8/88 (2006.01)
B65D 81/32 (2006.01)

(52) U.S. Cl.
CPC .............. A61K 8/84 (2013.01); A61K 8/36 (2013.01); A61K 8/4913 (2013.01); A61K 8/817 (2013.01); A61K 8/88 (2013.01); A61Q 5/002 (2013.01); B65D 81/32 (2013.01); A61K 2800/882 (2013.01); A61K 2800/884 (2013.01)

(58) Field of Classification Search
None
See application file for complete search history.

(56) References Cited

U.S. PATENT DOCUMENTS

| 2,874,126 | A | * | 2/1959 | Epstein | .................... A61K 8/39 |
| | | | | | 510/126 |
| 4,637,892 | A | * | 1/1987 | Merryman | ........... C11D 3/0031 |
| | | | | | 134/39 |
| 4,713,236 | A | | 12/1987 | Hoover et al. | |
| 8,105,393 | B2 | * | 1/2012 | Suddaby | .................. A61K 8/19 |
| | | | | | 132/202 |

| 2002/0172650 | A1 | * | 11/2002 | Cannell | .................... A61K 8/60 |
| | | | | | 424/70.2 |
| 2005/0129646 | A1 | * | 6/2005 | Vic | .......................... A61K 8/02 |
| | | | | | 424/70.11 |
| 2009/0269295 | A1 | * | 10/2009 | Benabdillah | ............. A61K 8/06 |
| | | | | | 424/70.9 |

FOREIGN PATENT DOCUMENTS

| FR | 2289167 A2 | 5/1976 |
| FR | 2910276 A1 | 6/2008 |
| GB | 1524966 * | 9/1975 |
| JP | 57-159706 A | 10/1982 |
| KR | 10-2013-0114468 | 10/2013 |
| WO | 2008/156327 A2 | 12/2008 |

OTHER PUBLICATIONS

International Search Report for PCT/FR2015/050412, dated May 7, 2015.
Database WPI Week 198320, Thomson Scientific, London, GB; AN 1983-47418K, XP002731377.
Database WPI Week 201414, Thomson Scientific, London, GB; AN 2013-T28949, XP002731374.
Gottschalck, Tara E. et al., "Polylysine," International Cosmetic Ingredient Dictionary and Handbook, 2012, Personal Care Products Council, Washington, D.C., XP002731375, vol. 2, pp. 2540-2541.
Gottschalck, Tara E. et al., "Vinylamine/vinylformamide Copolymer," International Cosmetic Ingredient Dictionary and Handbook, 2012, Personal Care Products Council, Washington, D.C., XP002731376, vol. 3, p. 3462.
Woodard, "Aziridine Chemistry—Applications for Cosmetics," J. Soc. Cosmet. Chem, 23, 1972, pp. 593-601.
English language Abstract for KR10-2013-0114468A, Oct. 18, 2013.
English language Abstract for JPS57-159706, Oct. 1, 1982.

(Continued)

Primary Examiner — Jennifer A Berrios
(74) Attorney, Agent, or Firm — The Marbury Law Group, PLLC

(57) ABSTRACT

The invention relates to a cosmetic process for treating keratin fibers, comprising a step of applying, to the keratin fibers, a first cosmetic composition comprising an amino polymer comprising a primary amine group, followed by a step of applying a second cosmetic composition comprising an activated ester of formula R—C(O)OA$_1$ in which R denotes a C$_5$-C$_{21}$ alkyl group, and A$_1$ denotes a particular reactive group and in particular a succinimide group.

The invention also relates to a kit comprising a first cosmetic composition comprising said amino polymer and a second cosmetic composition comprising said activated ester, the first and second compositions each been packaged in a separate packaging assembly.

The process gives the treated damaged fiber a long-lasting hydrophobic surface state, the hydrophobicity effect being persistent after one or more shampoo washes, while at the same time affording a good cosmetic feel.

16 Claims, No Drawings

(56) References Cited

OTHER PUBLICATIONS

English language Abstract for FR2910276A1, Jun. 27, 2008.
English language Abstract for FR2289167A2, May 28, 1976.

* cited by examiner

METHOD FOR TREATING KERATIN FIBRES WITH AN AMINO POLYMER AND AN ACTIVATED ESTER

CROSS REFERENCE TO RELATED APPLICATION

This is a national stage application of PCT/FR2015/050412, filed internationally on Feb. 20, 2015, which claims priority to French Application No. 1451536, which was filed on Feb. 26, 2014, both of which are incorporated by reference herein in their entireties.

The present invention relates to a process for treating keratin fibers comprising the application to the fibers of a particular amino polymer and of a particular activated ester. It also relates to a kit for implementing such a process.

Hair is generally damaged and embrittled by the action of chemical treatments such as dyeing, bleaching, permanent-waving, relaxing and repeated washing.

It is known that certain hair treatments such as dyeing, bleaching, permanent-waving and relaxing can attack the hair fiber and give rise in particular to the loss of some of the constituents thereof that are present in the natural state, in particular fatty acids such as 18-methyleicosanoic acid. The hair is thereby damaged and becomes sensitive.

The damaged fiber has an electrostatic nature, making it difficult to correctly shape the hair, in particular during combing or brushing. Furthermore, the damaged fiber has a more hydrophilic nature, making it very sensitive to water: the fiber has a tendency to swell and to frizz on contact with ambient moisture, and under these conditions does not ensure good hold of the hairstyle.

It is known that the cosmetic qualities of the hair may be improved by applying various compositions based on active agents or polymers for imparting various properties thereto, such as sheen, ease of disentangling, body, suppleness, liveliness or softness. To obtain good efficacy, these active agents should, of course, have a certain affinity for keratin fibers.

WO 2008/156 327 discloses a composition comprising lipids bearing functional groups, which, after application to the hair or the skin, are covalently bonded to the surface of the keratin materials. The functional groups are, for example, hydroxy-succinimidyl ester groups. The lipids, for their part, are $C_8$-$C_{26}$ fatty acids. However, the hydrophobicity effect obtained at the surface of the hair fades out in the course of successive shampoo washes and does not show satisfactory persistence on shampooing.

Moreover, the application of treating polymers to the hair may be harmful to the maintenance of a good feel: the treated hair is charged, feels coarse, is not smooth, is grating and is sparingly cosmetic.

Also known from document WO2008/156327 is a process for treating hair by application of an activated ester which gives the treated hair a surface hydrophobicity, for damage repair and prevention, in order to obtain a shiny, silky effect, and a coating, and with a semi-permanent conditioning effect, in particular which is persistent after shampooing.

Document KR2012-0036877 also describes a process for treating hair with a similar activated ester that imparts sheen, hydration and resistance to damage.

However, these treatments do not make it possible to obtain optimum hydrophobicity and persistence properties. There is thus a need for a hair treatment process that makes it possible to obtain improved hydrophobicity and persistence properties.

The object of the present invention is to propose a cosmetic process for treating keratin fibers, in particular the hair, making it possible to restore to a damaged fiber the surface physicochemical properties of a natural fiber, and to do so in a long-lasting manner.

A subject of the invention is thus a non-therapeutic cosmetic process for treating keratin fibers, comprising, in the following order:

a step of applying, to the keratin fibers, a first cosmetic composition comprising an amino polymer as defined below, followed by a step of applying a second cosmetic composition comprising an activated ester as defined below.

The treatment process is in particular a process for caring for keratin materials.

A subject of the invention is also a kit comprising:

a first cosmetic composition comprising an amino polymer as defined below and a second cosmetic composition comprising an activated ester as defined below, the first and second compositions each being packaged in a separate packaging assembly.

The composition packaging assembly is, in a known manner, any packaging that is suitable for storing cosmetic compositions (in particular a bottle, tube, spray bottle or aerosol bottle).

Such a kit allows the process for treating keratin materials according to the invention to be performed.

Polymers comprising a primary amine group, such as polyethyleneimines, poly(allylimine)s, for improving the conditioning properties of the hair are known from documents U.S. Pat. No. 4,713,236, FR2289167, FR2910276.

The process according to the invention allows the damaged fiber to regain a hydrophobic surface state close to that of natural hair, and to do so in a long-lasting manner, the hydrophobicity effect being persistent after one or more shampoo washes performed on the treated keratin fibers. The general appearance of the hair is improved, the treated hair is less electrostatic, has less body and less frizziness on contact with ambient moisture, thus contributing to good shaping of the hair, in particular of fine hair. The treated hair also has a good, soft, non-coarse cosmetic feel.

In particular, as shown by example 1, the process according to the invention makes it possible to obtain optimum improved hydrophobicity and persistence properties, while at the same time having a good feel. Application solely of the activated ester to the hair does not make it possible to achieve the optimum hydrophobicity property, and application solely of the amino polymer gives a charged, coarse and thus sparingly cosmetic feel.

The process according to the invention uses a first cosmetic composition comprising an amino polymer chosen from amino polymers comprising primary amine groups. They are polymers resulting from the polymerization of monomers, the polymer comprising at least 2 primary amine groups —$NH_2$.

The amino polymer can in particular be chosen from:

poly(($C_2$-$C_5$)alkyleneimine)s, and in particular polyethyleneimines and polypropyleneimines, in particular linear or branched polyethyleneimines (for example sold under the reference 46,852-3 by the company Aldrich Chemical);

poly(allylamine) for example that sold under the reference 47,913-6 by the company Aldrich Chemical or by the company Beckmann-Kenko);

polyvinylamines and copolymers thereof, in particular with vinylamides; mention may in particular be made of vinylamine/vinylformamide copolymers (the vinylamine content possibly ranging from 30% to 90% by weight of the total weight of the polymer), such as those sold under the name Lupamin® 9030 by the company BASF;

polyamino acids which have $NH_2$ groups, such as polylysine; for example that sold by the company JNC Corporation;

aminodextran, such as that sold by the company CarboMer Inc; vinylamine/vinyl alcohol copolymers, such as those sold by the company Chemwill;

acrylamidopropylamine polymers;

chitosans, such as those sold under the names Zenvivo® Protect and Zenvivo Aqua by the company Clariant.

Preferably, the amino polymer is chosen from:
polyethyleneimines;
poly(allylamine);
polylysine;
vinylamine/vinylformamide copolymers;
chitosans.

Preferentially, the amino polymer is chosen from poly (allylamine), poly(vinylamine/vinylformamide) copolymers and chitosans.

More preferentially, the amino polymer is a poly(allylamine).

Advantageously, the amino polymer has a weight-average molecular weight ranging from 200 to 1 000 000 g/mol, preferably ranging from 300 to 500 000 g/mol.

Preferably, the amino polymer is water-soluble. The term "water-soluble polymer" means a polymer with a solubility in water, at 25° C., of at least 0.1 g/l.

The amino polymer may be present in the first composition in a content ranging from 0.001% to 20% by weight, relative to the total weight of the composition, preferably ranging from 0.001% to 10% by weight, preferentially ranging from 0.001% to 5% by weight and more preferentially ranging from 0.1% to 5% by weight.

The second composition comprises an activated ester corresponding to formula (I):

R—C(O)OA1         (I)

in which R denotes a $C_5$-$C_{21}$, preferably $C_9$-$C_{17}$, preferentially $C_{11}$-$C_{15}$ alkyl group; $A_1$ denotes a reactive group chosen from:

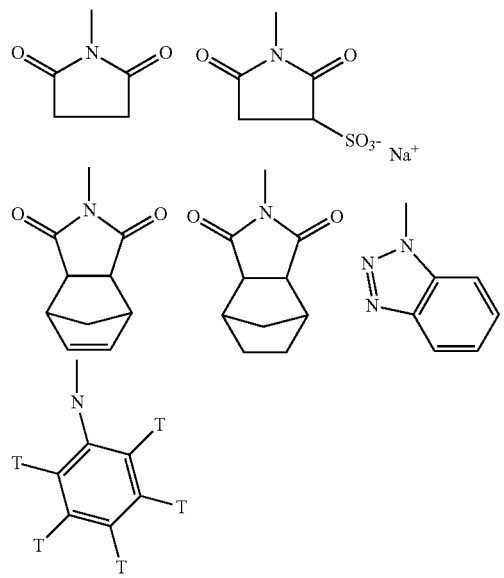

with T=independently H or F or Cl.

These activated ester compounds are known from the literature.

Preferably, A1 denotes the reactive group

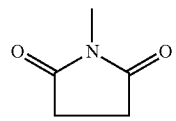

and R denotes a $C_9$-$C_{17}$, preferentially $C_{11}$-$C_{15}$, alkyl group.

The activated ester is preferably chosen from: the ester of lauric acid and of N-hydroxysuccinimide, and the ester of palmitic acid and of N-hydroxysuccinimide. Advantageously, the activated ester is the ester of palmitic acid and of N-hydroxysuccinimide.

The activated ester may be present in the second composition in a content ranging from 0.1% to 5% by weight, preferably ranging from 0.5% to 4% by weight and preferentially ranging from 1% to 4% by weight, relative to the total weight of the composition.

The cosmetic compositions used according to the invention contain a physiologically acceptable medium i.e. a medium that is compatible with human keratin materials such as the skin (of the body, face, around the eyes or the scalp), the hair, the eyelashes, the eyebrows, bodily hair, the nails or the lips.

Advantageously, the first cosmetic composition used according to the invention comprises a physiologically acceptable non-aqueous medium. It may be constituted, for example, of water or of a mixture of water and of at least one cosmetically acceptable organic solvent. Examples of organic solvents that may be mentioned include $C_2$-$C_4$ lower alcohols, such as ethanol and isopropanol; polyols, in particular those containing from 2 to 6 carbon atoms, for instance glycerol, propylene glycol, butylene glycol, pentylene glycol, hexylene glycol, dipropylene glycol or diethylene glycol; polyol ethers, for instance 2-butoxyethanol, propylene glycol monomethyl ether, diethylene glycol monomethyl ether or monoethyl ether, and short esters such as ethyl acetate or butyl acetate; and mixtures thereof.

Preferably, the cosmetic composition comprises from 50% to 99.5% by weight of water relative to the weight of the composition.

Advantageously, the second cosmetic composition used according to the invention comprises a physiologically acceptable non-aqueous medium. It may be constituted, for example, by one, or more cosmetically acceptable organic solvents, such as those described previously, or alternatively one or more common cosmetic oils.

The compositions used according to the invention may also contain one or more cosmetic additives chosen from nonionic, anionic, cationic and amphoteric surfactants, vitamins and provitamins, including panthenol, sunscreens, fillers, colorants, nacreous agents, opacifiers, sequestrants, film-forming polymers, plasticizers, thickeners, oils, antioxidants, antifoams, moisturizers, emollients, penetrants, fragrances and preserving agents.

The compositions used according to the invention may be in any galenical form conventionally used for application to the hair and in particular in the form of aqueous solutions, aqueous-alcoholic solutions, oil-in-water (O/W), water-in-oil (W/O) or multiple (triple: W/O/W or O/W/O) emulsions, aqueous gels or aqueous-alcoholic gels. These compositions are prepared according to the usual methods. Preferably, the composition is in the form of an aqueous or aqueous-alcoholic solution or gel.

The process according to the invention may be carried out on keratin fibers, in particular hair, which is dry or wet. Preferentially, the process is performed on dry keratin fibers, in particular hair.

After application to the keratin fibers of the cosmetic composition comprising the amino polymer and/or the activated ester, the applied composition may be left to stand on the fibers for a time ranging from 1 to 60 minutes, preferably ranging from 2 to 50 minutes, preferentially ranging from 5 to 30 minutes. The leave-on time may take place at a temperature ranging from 15° C. to 45° C., preferably at ambient temperature (25° C.).

The cosmetic compositions described previously are advantageously applied to the keratin fibers in an amount ranging from 0.1 to 10 grams and preferably from 0.2 to 5 grams of composition per gram of keratin fibers.

After application of the cosmetic compositions to the keratin fibers, the latter may be drained dry to remove the excess composition or washed with water.

After the treatment, the keratin fibers may be optionally rinsed with water or washed with a shampoo. The keratin fibers are then optionally dried with a hairdryer or a hood or in the open air.

The treatment process according to the invention is preferably performed on keratin fibers, in particular hair, which are sensitized, such as artificially dyed fibers (keratin fibers dyed following a direct dyeing process or via an oxidation dyeing process), bleached, relaxed or permanent-waved fibers.

The treatment process according to the invention may be performed before, during and/or after an additional process of cosmetic treatment of the keratin fibers, such as a process for temporarily shaping (shaping with curlers, a crimping iron or a straightening iron) or a process for durably shaping (permanent-waving or relaxing) the keratin fibers.

The treatment process may be performed as a pre-treatment to a dyeing or relaxing process and/or a permanent-waving process so as to cosmetically protect the keratin fibers against these treatments. In other words, this process is performed to preserve the cosmetic properties of the keratin fibers before a cosmetic treatment process as described previously.

Preferentially, the treatment process is performed as a post-treatment to a bleaching, artificial dyeing or relaxing process and/or a permanent-waving process so as to repair said fibers.

The process according to the invention is preferably performed on the hair.

The examples that follow are given as illustrations of the present invention.

The amounts indicated in the examples are expressed as weight percentages.

EXAMPLE 1

Locks of sensitized hair (bleaching SA 20%) were used.
Compositions Prepared

|  | Compositions | | |
|---|---|---|---|
|  | A1 | A2 | B |
| Poly(allylamine)* | 0.5 | 3 |  |
| Ester of palmitic acid and of N-hydroxysuccinimide |  |  | 3 |
| Water | qs 100 | qs 100 |  |
| Butyl acetate/ethanol (50/50) |  |  | qs 100 |

*poly(allylamine) from Beckmann-Kenko

The tests were carried out on a lock of hair.

Composition A1 or A2 was applied to wet locks of hair (1.5 g of composition per gram of hair), then the locks were placed in an oven at 60° C. for 30 minutes, with said locks being turned over after 15 minutes.

Composition B (1.5 g of composition per gram of hair) was, then applied to the locks. The locks were then placed in an oven at 40° C. for 30 minutes, with said locks being turned over after 15 minutes.

The locks were then rinsed with running water; they were wrung out and then dried under a hood for 15 minutes at 80° C.

For some locks, 5 shampooing operations were carried out according to the following protocol:

The treated locks were washed with a DOP camomile shampoo, in a proportion of 0.4 g of shampoo per gram of hair, at a temperature of 38° C.

Moisten the lock for 5 seconds with water. Apply the shampoo, massaging the lock from the root to the end for 15 seconds. Rinse with water for 10 seconds. Wring out. Repeat the steps of applying the shampoo followed by rinsing. Dry the locks for 10 minutes per gram of hair at 60° C. with a hairdryer.

For each lock of treated hair, wettability of the hair was measured (measurements described in particular in the book The Science of Hair Care by C. Bouillon and J. Wilkinson—2nd edition 2005—Chapter 12: Evaluation of product efficacy—page 407).

The measurement of the wettability of a hair consists in immersing a piece of hair in a crystallizing dish of ultra-pure water and in measuring the force generated by the displacement of the hair fiber during its immersion (wetting force) and during its withdrawal from the water. This force varies as a function of the affinity of the hair for the liquid and makes it possible to assess the surface state of the fiber.

A K14 tensiometer from the company Krüss was used under the following operating conditions:
Approach speed: 4 mm/minute.
Measuring speed: 2 mm/minute.
Balance sensitivity: 10 μg
Waiting time after immersion: 2 seconds
Immersion depth: 2 mm.

The hairs raised on a holder are still oriented in the same direction, i.e. end downwards, root upwards.

For each treatment, 20 samples are measured under the same conditions.

The hairs were left to regulate overnight in a glove box at 25° C. and 45% hygrometry before measuring them.

Data Processing

The wetting force (F in newtons) is determined according to the following formula:

$$F = L \times \sigma \times \cos\theta$$

L being the perimeter of the hair (in meters)
θ: contact angle
Σ: surface tension of pure water=72.75 mN/m at atmospheric pressure The wetting force expressed in mN was transformed into μg, and then normalized relative to the mean perimeter of the fibers.

From the 20 measurements for each lock, the mean value and its confidence interval are calculated. The lower the wetting force, the more hydrophobic the treated hair.

The feel of the treated lock (more or less coarse feel to the touch) was also evaluated.

The following results were obtained.

| Lock/treatment | Feel | Wetting force (µg) |
|---|---|---|
| Non-treated control lock | Correct feel | 5.39 ± 0.36 |
| Lock 1 treated with composition B | Correct feel | 3.59 ± 0.53 |
| Lock 2 treated with composition A1 | Coarser feel | −2.30 ± 0.35 |
| Lock 3 treated with composition A1 + 5 shampooing operations | Coarse feel | −6.28 ± 0.51 |
| Lock 4 treated with composition A1 + 10 shampooing operations | Coarse feel | −5.96 ± 0.82 |
| Lock 5 treated with composition A1 then B | Correct feel | −3.49 ± 0.65 |
| Lock 6 treated with composition A1 then B + 5 shampooing operations | Correct feel | −5.03 ± 0.43 |
| Lock 7 treated with composition A1 then B + 10 shampooing operations | Correct feel | −4.76 ± 0.38 |
| Lock 8 treated with composition A2 | Coarse, charged feel | −2.61 ± 0.60 |
| Lock 9 treated with composition A2 + 5 shampooing operations | Coarse, charged feel | −6.34 ± 1.30 |
| Lock 10 treated with composition A2 then B | Correct feel | −4.43 ± 0.57 |
| Lock 11 treated with composition A2 then B + 5 shampooing operations | Correct feel | −4.72 ± 0.62 |

The results obtained show that locks Nos 5, 6, 7, 10 and 11 treated with the process according to the invention have the best surface-hydrophobicity and good-feel properties.

EXAMPLE 2

The following basecoat composition is applied to a lock of sensitized hair (type SA 20) (contents in weight percentage):

| Polyethyleneimine of molecular weight 423 g/mol (reference 46,853-3 from Aldrich) | 0.5% |
|---|---|
| Water | qs 100% |

It is left to stand on the lock for 30 minutes at 60° C.

The excess product is wiped off and then the following topcoat composition is applied:

| ester of palmitic acid and of N-hydroxysuccinimide | 3% |
|---|---|
| butyl acetate/ethanol (50/50 weight/weight) | qs 00% |

It is left to stand on the lock for 30 minutes.

The treated hair is rinsed and then shampooing is performed (DOP camomile) and the hair is dried with a hairdryer.

The treated hair after application of the 2 compositions exhibits an improved surface hydrophobicity which is persistent after shampooing, and also a good feel.

EXAMPLE 3

The following basecoat composition is applied to a lock of sensitized hair (type SA 20) (contents in weight percentage):

| Poly(vinylamine/vinylformamide) copolymer (LUPAMIN ® 9030 from BASF) | 0.5% |
|---|---|
| Water | qs 100% |

It is left to stand on the lock for 30 minutes at 60° C.

The excess product is wiped off and then the following topcoat composition is applied:

| ester of palmitic acid and of N-hydroxysuccinimide | 3% |
|---|---|
| butyl acetate/ethanol (50/50 weight/weight) | qs 00% |

It is left to stand on the lock for 30 minutes.

The treated hair is rinsed and then shampooing is performed (DOP camomile) and the hair is dried with a hairdryer.

The treated hair after application of the 2 compositions exhibits an improved surface hydrophobicity which is persistent after shampooing, and also a good feel.

EXAMPLE 4

The following basecoat composition was applied to a lock of sensitized hair (type SA20) (contents in weight percentage):

| Polylysine (Polylysine 25% solution from JNC) (reference 47,913-6 from Aldrich) | 0.5% AM |
|---|---|
| Water | qs 100% |

It is left to stand on the lock for 30 minutes at 60° C.

The excess product is wiped off and then the following topcoat composition is applied:

| ester of palmitic acid and of N-hydroxysuccinimide | 3% |
|---|---|
| butyl acetate/ethanol (50/50 weight/weight) | qs 00% |

It is left to stand on the lock for 30 minutes.

The treated hair is rinsed and then shampooing is performed (DOP camomile) and the hair is dried with a hairdryer.

The treated hair after application of the 2 compositions exhibits an improved surface hydrophobicity which is persistent after shampooing, and also a good feel.

The invention claimed is:

1. A process for treating keratin fibers, the method comprising:
   applying to the fibers:
      a first cosmetic composition comprising at least one amino polymer comprising at least one primary amine group, wherein the at least one amino polymer is chosen from poly((C$_2$-C$_5$)alkyleneimine)s, poly(allylamine), polyvinylamines or copolymers thereof, polyamino acids comprising NH$_2$ groups, aminodextran, vinylamine/vinyl alcohol copolymers, acrylamidopropylamine polymers, or chitosans, and subsequently, a second cosmetic composition comprising at least one activated ester of formula (I) below:

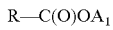

wherein:
R is a C$_9$-C$_{17}$ alkyl group; and
A$_1$ is the reactive group;

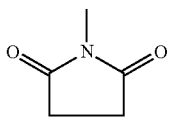

and
heating the fibers.

2. The process according to claim 1, wherein the at least one amino polymer is chosen from:
polyethyleneimines;
poly(allylamine);
polylysine;
vinylamine/vinylformamide copolymers; or
chitosans.

3. The process according to claim 1, wherein the at least one amino polymer is a poly(allylamine).

4. The process according to claim 1, wherein the at least one amino polymer has an average molecular weight ranging from about 200 to about 1,000,000 g/mol.

5. The process according to claim 4, wherein the at least one amino polymer has an average molecular weight ranging from about 300 to about 500,000 g/mol.

6. The process according to claim 1, wherein the at least one amino polymer has a solubility in water, at 25° C., of at least 0.1 g/L.

7. The process according to claim 1, wherein the at least one amino polymer is present in the first composition in an amount ranging from about 0.001% to about 20% by weight, relative to the total weight of the first composition.

8. The process according to claim 7, wherein the at least one amino polymer is present in the first composition in an amount ranging from about 0.001% to about 10% by weight, relative to the total weight of the first composition.

9. The process according to claim 7, wherein the at least one amino polymer is present in the first composition in an amount ranging from about 0.001% to about 5% by weight, relative to the total weight of the first composition.

10. The process according to claim 1, wherein the at least one activated ester of formula (I) is chosen from the ester of lauric acid and of N-hydroxysuccinimide, or the ester of palmitic acid and of N-hydroxysuccinimide.

11. The process according to claim 1, wherein the at least one activated ester of formula (I) is present in the second composition in an amount ranging from about 0.1% to about 5% by weight, relative to the total weight of the second composition.

12. The process according to claim 11, wherein the at least one activated ester of formula (I) is present in the second composition in an amount ranging from about 0.5% to about 4% by weight, relative to the total weight of the second composition.

13. The process according to claim 11, wherein the at least one activated ester of formula (I) is present in the second composition in an amount ranging from about 1% to about 4% by weight, relative to the total weight of the second composition.

14. The process according to claim 1, further comprising leaving the first composition and second composition on the fibers for a time ranging from about 1 to about 60 minutes, at a temperature ranging from about 15° C. to about 45° C.

15. The process according to claim 1, wherein the first composition further comprises water in an amount ranging from 50% to 99.5% by weight, relative to the total weight of the first composition.

16. The process according to claim 1, wherein the second composition further comprises a physiologically acceptable non-aqueous medium.

* * * * *